United States Patent [19]

Senn-Bilfinger

[11] Patent Number: 5,668,131
[45] Date of Patent: Sep. 16, 1997

[54] SUBSTITUTED AMINOALKYLAMINOPYRIDINES

[75] Inventor: Jörg Senn-Bilfinger, Constance, Germany

[73] Assignee: BYK Gulden Lomberg Chemische Fabrik GmbH, Constance, Germany

[21] Appl. No.: 652,505

[22] PCT Filed: Nov. 26, 1994

[86] PCT No.: PCT/EP94/03911

§ 371 Date: May 31, 1996

§ 102(e) Date: May 31, 1996

[87] PCT Pub. No.: WO95/15324

PCT Pub. Date: Jun. 8, 1995

[30] Foreign Application Priority Data

Dec. 1, 1993 [CH] Switzerland ............... 3581/93

[51] Int. Cl.$^6$ .............. C07D 401/12; C07D 401/14; A61K 31/415; A61K 31/44

[52] U.S. Cl. .............. 514/234.5; 514/255; 514/303; 514/307; 514/314; 514/318; 514/338; 544/124; 544/360; 546/118; 546/148; 546/164; 546/165; 546/193; 546/273.7

[58] Field of Search .............. 546/118, 148, 546/164, 165, 193, 273.7; 544/124, 360; 514/234.5, 255, 303, 338, 307, 314, 318

[56] References Cited

FOREIGN PATENT DOCUMENTS

| 2136993 | 12/1993 | Canada. |
| 184 322 | 6/1986 | European Pat. Off. . |
| 567 643 | 11/1993 | European Pat. Off. . |

Primary Examiner—Mukund J. Shah
Assistant Examiner—Deepak Rao
Attorney, Agent, or Firm—Jacobson, Price, Holman & Stern, PLLC

[57] ABSTRACT

Compounds of formula I

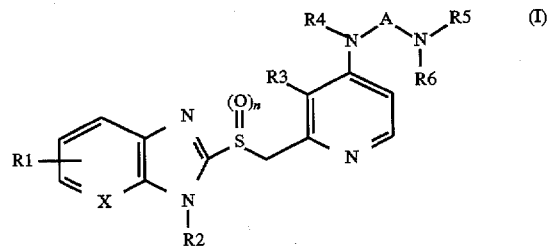

wherein R1, R2, R3, R4, R5, R6, X, n and A have the meanings as given in the description, can be used for combatting Helicobacter bacteria.

11 Claims, No Drawings

SUBSTITUTED AMINOALKYLAMINOPYRIDINES

This application is a 371 of PCT/EP94/03911 filed on Nov. 26, 1994.

AREA OF APPLICATION OF THE INVENTION

The invention relates to compounds which are intended to be used in the pharmaceutical industry as active substance for the production of pharmaceuticals.

KNOWN TECHNICAL BACKGROUND

International Patent Application WO92/12976 describes 2-(pyridylmethylthio- and -sulfinyl)benzimidazoles which are substituted in a particular manner and which are said to be active against helicobacter bacteria, and for which it is furthermore disclosed that they are intended to be suitable for preventing and treating a whole range of gastric disorders.

DESCRIPTION OF THE INVENTION

The invention relates to compounds of formula I (see appended sheet of formulae) in which R1 is hydrogen, 1-4C-alkyl, 1-4C-alkoxy, halogen, trifluoromethyl, wholly or predominantly fluorine-substituted 1-4C-alkoxy, chlorodifluoromethoxy or 2-chloro-1,1,2-trifluoroethoxy, R2 is hydrogen or 1-4C-alkyl, R3 is halogen or 1-4C-alkyl, R4 is 1-7C-alkyl, A is 1-7C-alkylene, X is N or CH, and n is the number 0, 1 or 2, and in which R5 is 1-7C-alkyl, 3-8C-cycloalkyl or Ar-1-4C-alkyl and R6 is 1-7C-alkyl, 3-8C-cycloalkyl or Ar-1-4C-alkyl, where Ar is phenyl, furyl, naphthyl, tetrahydronaphthyl, or phenyl which is substituted by R7, R8 and R9, or in which R5 and R6 together represent, with inclusion of the nitrogen atom to which both are bonded, an unsubstituted or substituted heterocyclic ring which is selected from the group consisting of pyrrolidine, piperidine, piperazine, morpholine, indoline, octahydro-1H-indole, 1,2,3,4-tetrahydroquinoline, 1,2,3,4-tetrahydroisoquinoline, decahydroquinoline and decahydroisoquinoline, where a substituted pyrrolidino radical is substituted by one or two identical or different substituents selected from the group consisting of
1-4C-alkyl,
1-4C-alkoxy,
1-4C-alkoxy-1-4C-alkyl,
1-4C-alkoxycarbonyl,
1-4C-alkylcarbonyloxy,
hydroxy-1-4C-alkyl,
hydroxyl and
carboxyl, a substituted piperidino radical is substituted by one, two or three identical or different substituents selected from the group consisting of
1-4C-alkyl,
GEM.-di-1-4C-alkyl,
1-4C-alkoxy,
1-4C-alkoxy-1-4C-alkyl,
1-4C-alkoxycarbonyl,
1-4C-alkylcarbonyl,
1-4C-alkylcarbonyl-1-4C-alkyl,
hydroxy-1-4C-alkyl,
dihydroxy-1-4C-alkyl,
di-1-4C-alkylamino,
di-1-4C-alkylamino-1-4C-alkyl,
pyrrolidino,
piperidino,
pyrrolidinyl-1-4C-alkyl,
piperidinyl-1-4C-alkyl,
carbamoyl,
di-1-4C-alkylaminocarbonyl,
piperidinocarbonyl,
morpholinocarbonyl,
phenyl,
phenyl substituted by R7, R8 and R9,
phenyl-1-4C-alkyl,
benzoyl,
benzoyl substituted by halogen,
formyl,
carboxyl,
cyano,
hydroxyl,
halogen and
sulfo, a substituted piperazino radical can be substituted in position 2, 3, 5 or 6 by a 1-4C-alkyl radical and is substituted in position 4 by a substituent selected from the group consisting of
1-4C-alkyl,
3-7C-cycloalkyl,
3-7C-cycloalkyl-1-4C-alkyl,
1-4C-alkoxycarbonyl,
1-4C-alkoxycarbonyl-1-4C-alkyl,
hydroxy-1-4C-alkyl,
di-1-4C-alkylamino-1-4C-alkyl,
halo-1-4C-alkyl,
carbamoyl,
phenyl,
phenyl substituted by R7, R8 and R9,
phenyl-1-4C-alkyl,
phenyl-1-4C-alkyl substituted by R7, R8 and R9 in the phenyl radical,
naphthyl,
benzhydryl and
benzhydryl substituted by halogen, a substituted morpholino radical is substituted by one or two identical or different 1-4C-alkyl radicals, a substituted 1-indolinyl radical can be substituted in position 2 and/or 3 by a carboxyl group or by one or two identical or different 1-4C-alkyl radicals, and can be substituted in the benzo moiety by one or two identical or different substituents selected from the group consisting of 1-4C-alkyl, halogen and nitro, a substituted 1,2,3,4-tetrahydroquinoline radical is substituted by one or two identical or different substituents selected from the group consisting of 1-4C-alkyl and halogen, a substituted 1,2,3,4-tetrahydroisoquinoline radical can be substituted on positions 1, 3 and/or 4 by one or two identical or different substituents selected from the group consisting of 1-4C-alkyl, carboxyl, phenyl, phenyl-1-4C-alkyl or phenyl which is substituted by R7, R8 and R9 in the phenyl radical, and can be substituted on the benzo moiety by one or two substituents selected from the group consisting of hydroxyl, 1-4C-alkoxy and di-1-4C-alkylamino, and where R7 is hydrogen, 1-4C-alkyl, 1-4C-alkoxy, 1-4C-alkylcarbonyl, halogen, 1-4C-alkylamino or nitro, R8 is hydrogen, 1-4C-alkyl, 1-4C-alkoxy, halogen or nitro, and R9 is hydrogen or trifluoromethyl, and the salts of these compounds.

1-4C-Alkyl stands for straight-chain or branched alkyl radicals with 1 to 4 carbon atoms. Examples which may be mentioned are the butyl, isobutyl, sec-butyl, tert-butyl, propyl, isopropyl, ethyl and methyl radicals.

1-4C-Alkoxy stands for a radical which, besides the oxygen atom, contains one of the abovementioned 1-4C-alkyl radicals. Examples which may be mentioned are the methoxy and ethoxy radicals.

Halogen for the purpose of the present invention is bromine, chlorine and fluorine.

Examples of wholly or predominantly fluorine-substituted 1-4C-alkoxy which may be mentioned are the 1,2,2-trifluoroethoxy, the 2,2,3,3,3-pentafluoropropoxy, the perfluoroethoxy and, in particular, the 1,1,2,2-tetrafluoroethoxy, the trifluoromethoxy, the 2,2,2-trifluoroethoxy and the difluoromethoxy radicals.

1-7C-Alkyl stands for straight-chain and branched alkyl radicals with 1 to 7 carbon atoms. Examples which may be mentioned are the heptyl, hexyl, neopentyl, isopentyl, pentyl, butyl, isobutyl, sec-butyl, tert-butyl, propyl, isopropyl, ethyl and methyl radicals.

1-7C-Alkylene stands for straight-chain or branched 1-7C-alkylene radical, for example the methylene ($-CH_2-$), ethylene ($-CH_2-CH_2-$), trimethylene ($-CH_2-CH_2-CH_2-$), tetramethylene ($-CH_2-CH_2-CH_2-CH_2-$), 1,2-dimethylethylene [$-CH(CH_3)-$], 1,1-dimethylethylene [$-C(CH_3)_2-CH_2-$], 2,2-dimethylethylene $-CH_2-C(CH_3)_2-$], isopropylidene [$-C(CH_3)_2-$], 1-methylethylene [$-CH(CH_3)CH_2-$], pentamethylene ($-CH_2-CH_2-CH_2-CH_2-CH_2-$), hexamethylene ($-CH_2-CH_2-CH_2-CH_2-CH_2-CH_2-$) and heptamethylene radicals ($-CH_2-CH_2-CH_2-CH_2-CH_2-CH_2-CH_2-$).

3-8C-Cycloalkyl stands for the cyclopropyl, cyclobutyl, cyclopentyl, cyclohexyl, cycloheptyl and cyclooctyl radicals.

Ar-1-4C-alkyl stands for one of the abovementioned Ar-substituted 1-4C-alkyl radical. Examples which may be mentioned are the phenethyl, the benzyl, the 2-furylmethyl (=furfuryl) and the 1-naphthylmethyl radicals.

1-4C-Alkoxy-1-4C-alkyl stands for one of the abovementioned 1-4C-alkyl radicals which is substituted by one of the abovementioned 1-4C-alkoxy radicals. Examples which may be mentioned are the methoxymethyl, the methoxyethyl ethyl radicals and the butoxyethyl radical.

1-4C-Alkoxycarbonyl stands for a radical which, besides the carbonyl group, contains one of the abovementioned 1-4C-alkoxy radicals. Examples which may be mentioned are the methoxycarbonyl and the ethoxycarbonyl radicals.

1-4C-Alkylcarbonyloxy stands for a radical which, besides the carbonyloxy radical, contains one of the above 1-4C-alkyl radicals. An example which may be mentioned is the acetoxy radical.

Hydroxy-1-4C-alkyl stands for one of the abovementioned 1-4C-alkyl radicals which is substituted by hydroxyl. Examples which may be mentioned are the hydroxymethyl radical, the 2-hydroxyethyl radical or the 3-hydroxypropyl radical.

1-4C-Alkylcarbonyl stands for a radical which, besides the carbonyl group, contains one of the abovementioned 1-4C-alkyl radicals. An example which may be mentioned is the acetyl radical.

1-4C-Alkylcarbonyl-1-4C-alkyl stands for one of the abovementioned 1-4C-alkyl radicals which is substituted by one of the abovementioned 1-4C-alkylcarbonyl radicals. Examples which may be mentioned are the 2-oxopropyl radical (acetonyl radical) and the 2-oxobutyl radical.

Dihydroxy-1-4C-alkyl stands for one of the abovementioned 1-4C-alkyl radicals which is substituted by two hydroxyl groups. An example which may be mentioned is the 1,2-dihydroxyethyl radical.

Di-1-4C-alkylamino stands for an amino radical which is substituted by two identical or different abovementioned 1-4C-alkyl radicals. Examples which may be mentioned are the dimethylamino, the diethylamino and the diisopropylamino radicals.

Di-1-4C-alkylamino-1-4C-alkyl stands for one of the abovementioned 1-4C-alkyl radicals which is substituted by one of the abovementioned di-1-4C-alkylamino radicals. Examples which may be mentioned are the dimethylaminomethyl, the dimethylaminoethyl and the diethylaminoethyl radicals.

Pyrrolidinyl-1-4C-alkyl and piperidinyl-1-4C-alkyl stand for the abovementioned 1-4C-alkyl radicals which are substituted by a pyrrolidinyl and piperidinyl radical respectively. Examples which may be mentioned are the 2-pyrrolidinoethyl, the 2-piperidinoethyl, the piperidinomethyl and the 2-(4-piperidin-4-yl)ethyl radicals.

Di-1-4C-alkylaminocarbonyl stands for a radical which, besides the carbonyl group, contains one of the abovementioned di-1-4C-alkylamino groups. Examples which may be mentioned are the dimethylcarbamoyl and the diethylcarbamoyl radicals.

3-7C-Cycloalkyl-1-4C-alkyl stands for one of the abovementioned 1-4C-alkyl radicals which is substituted by one of the abovementioned 3-7C-cycloalkyl radicals. Examples which may be mentioned are the cyclopropylmethyl, the cyclohexylmethyl and the cyclohexylethyl radicals.

1-4C-Alkoxycarbonyl-1-4C-alkyl stands for one of the abovementioned 1-4C-alkyl radicals which is substituted by one of the abovementioned 1-4C-alkoxycarbonyl radicals. An example which may be mentioned is the ethoxycarbonylmethyl radical.

Halo-1-4C-alkyl stands for one of the abovementioned 1-4C-alkyl radicals which is substituted by one of the abovementioned halogen atoms. An example which may be mentioned is the 3-chloropropyl radical.

Examples which may be mentioned of phenyl radicals substituted by R7, R8 and R9 are the 3,4-dihydroxy-, 3-hydroxy-4-methoxy-, 3,4-dimethoxy-, 2-methoxy-, 2-ethoxy-, 3-methoxy-, 4-methoxy, 2-hydroxy-, 3-hydroxy-, 4-hydroxy-, 3,4-dihydroxy-, 4-acetyl-, 4-fluoro-, 4-chloro-, 2-chloro-, 3-chloro-, 3,4-dichloro-, 3-trifluoromethyl-, 2-trifluoromethyl-, 2-methyl-, 3-methyl-, 4-methyl-, 2,3-dimethyl-, 2,4-dimethyl-, 3,4-dimethyl-, 2,5-dimethyl-, 4-nitro-, 2,6-dinitro-4-trifluoromethyl- and 5-chloro-2-methylaminophenyl radicals.

Examples which may be mentioned of substituted pyrrolidino radicals are the 2-methoxymethylpyrrolidino, 2-methoxycarbonylpyrrolidino, 2-methylpyrrolidino, 2,5-dimethylpyrrolidino, 2-carboxypyrrolidino, 4-hydroxy-2-methoxycarbonylpyrrolidino, 4-hydroxy-2-ethoxycarbonylpyrrolidino, 2-(2-hydroxyethyl)pyrrolidino, 4-hydroxy-2-carboxypyrrolidino, 2-hydroxymethylpyrrolidino, 3-hydroxypyrrolidino and the 4-acetoxy-2-carboxypyrrolidino radicals.

Examples which may be mentioned of substituted piperidino radicals are the 3-hydroxypiperidino, 2-carboxypiperidino, 3-aminopiperidino, 4-[2-(4-piperidin-4-yl)ethyl]piperidino, 4-cyano-4-phenylpiperidino, 4,4-dihydroxypiperidino, 2-n-propylpiperidino, 5-ethyl-2-methylpiperidino, 2-dimethylaminomethylpiperidino, 2-(2-pyrrolidinoethyl)piperidino, 4-benzyl-4-hydroxypiperidino, 4-formyl-4-phenylpiperidino, 4-hydroxymethyl-4-phenylpiperidino, 4-n-propylpiperidino, 4-(3-phenylpropyl)piperidino, 4-dimethylaminopiperidino, 4-ethoxy-4-phenylpiperidino, 4-hydroxy-4-(4-fluorophenyl)piperidino, 2-(1-hydroxy)benzylpiperidino, 2-(1-hydroxy)-4-chlorobenzylpiperidino, 4-(1-pyrrolidinyl)piperidino, 4,4-dimethylpiperidino, 4-phenyl-4-propyloxypiperidino, 2,6-dimethylpiperidino, 3-hydroxy-2,6-dihydroxymethylpiperidino, 2,6-di(2-oxobutyl)piperidino, 4-hydroxypiperidino, 4-hydroxy-4-phenylpropylpiperidino, 4-(1-oxopropyl)- 4-phenylpiperidino, 4-(1-oxobutyl)-4-phenylpiperidino, 4-phenyl-4-propyloxycarbonylpiperidino, 4-phenyl-4-(1-piperidinylcarbonyl)piperidino, 4-carbamoyl-4-phenylpiperidino, 4-carbamoyl-4-dimethylaminopiperidino, 4-morpholinocarbonyl-4-phenylpiperidino, 4-carbamoylpiperidino, 4-[3-(4-piperidinyl)propyl]piperidino, 2-carboxy-5-hydroxypiperidino, 4-acetyl-4-phenylpiperidino, 2-ethyl-2-methylpiperidino, 4-ethoxycarbonyl-4-phenylpiperidino, 4-bromo-4-phenylpiperidino, 4-carboxy-4-phenylpiperidino, 4-hydroxy-4-(3-trifluoromethylphenyl)piperidino, 4-formylpiperidino, 4-carboxypiperidino, 4-(4-fluorobenzoyl)piperidino, 2-(1,2-dihydroxyethyl)piperidino, 2-(2-dimethylaminoethyl)piperidino, 4-(2-dimethylaminoethyl)piperidino, 4-(2-diethylaminoethyl)piperidino, 4-(4-chlorobenzoyl)piperidino, 4-(2-butyloxyethyl)-piperidino, 4-[2-(1-piperidinyl)ethyl]-piperidino, 2,3-dicarboxypiperidino, 2,4-dicarboxypiperidino, 2,6-dicarboxypiperidino, 4-sulfopiperidino, 2-ethoxycarbonylpiperidino, 2-methylpiperidino, 2,2,6,6-tetramethylpiperidino, 4-hydroxy-2,2,6,6-tetramethylpiperidino, 4-amino-2,2,6,6-tetramethylpiperidino, 2,6-dimethylpiperidino, 2-hydroxymethylpiperidino, 2-ethylpiperidino, 2-(2-hydroxyethyl)piperidino, 3-diethylcarbamoylpiperidino, 3-ethoxycarbonylpiperidino, 4-hydroxy-4-(4-chlorophenyl)piperidino, 4-(1-piperidinyl)piperidino and the 4-benzylpiperidino radicals.

Examples which may be mentioned of substituted piperazino radicals are the 4-methylpiperiazino, 4-[2-(2-trifluoromethylphenyl)ethyl]piperazino, 4-(3-chloropropyl)piperazino, 4-phenylpiperazino, 4-(2-methylphenyl)piperazino, 4-(2,3-dimethylphenyl)piperazino, 4-(2-chlorophenyl)piperazino, 4-(2-methoxyphenyl)piperazino, 4-(2-ethoxyphenyl)piperazino, 4-(3-chlorophenyl)piperazino, 4-(4-fluorophenyl)piperazino, 4-(4-chlorophenyl)piperazino, 4-(4-methoxyphenyl)piperazino, 4-carbamoylpiperazino, 3-methyl-4-(4-chlorophenyl)piperazino, 3-methyl-4-(4-methoxyphenyl)piperazino, 3-methyl-4-(4 -methylphenyl)piperazino, 4-(2,4-dimethylphenyl)piperazino, 4-(3,4-dichlorophenyl)piperazino, 4-(3,4-dimethylphenyl)piperazino, 4-(3-hydroxypropyl)piperazino, 3-methyl-4-phenylpiperazino, 3-methyl-4-(3-chlorophenyl)piperazino, 4-benzylpiperazino, 4-propylpiperazino, 4-(3-methylphenyl)piperazino, 4-(3-methoxyphenyl)piperazino, 4-(4-methylphenyl)piperazino, 4-(2,5-dimethylphenyl)piperazino, 4-benzhydrylpiperazino, 4-cyclopropylpiperazino, 4-cyclobutylpiperazino, 4-cyclopentylpiperazino, 4-cyclohexylpiperazino, 4-cycloheptylpiperazino, 4-n-butylpiperazino, 4-isobutylpiperazino, 4-tert-butylpiperazino, 4-dimethylaminomethylpiperazino, 4-(2-diethylaminoethyl)piperazino, 4-(3-trifluoromethylphenyl)piperazino, 4-(1-phenylethyl)piperazino, 4-ethoxycarbonylmethylpiperazino, 4-(2-phenylethyl)piperazino, 4-(2-cyclohexylethyl)piperazino, 4-(2-dimethylaminoethyl)piperazino, 4-(2-hydroxyphenyl)piperazino, 4-(3,4-dimethoxyphenyl)piperazino, 4-isopropylpiperazino, 3-methyl-4-(3-methoxyphenyl)piperazino, 4-(4-hydroxyphenyl)piperazino, 3-methyl-4-(3-methylphenyl)piperazino, 4-(3-hydroxyphenyl)piperazino, 4-(2,6-dinitro-4-trifluoromethylphenyl)piperazino, 4-(1-naphthyl)piperazino, 4-(2-hydroxyethyl)piperazino, 4-(4-nitrophenyl)piperazino, 4-(4-acetylphenyl)piperazino, 4-ethoxycarbonylpiperazino and the 4-(4-chlorobenzhydryl)piperazino radicals.

An example which may be mentioned of a substituted morpholino radical is the 3,5-dimethylmorpholino radical.

Examples which may be mentioned of substituted 1-indolinyl radicals are the 2-carboxy-1-indolinyl, 6-fluoro-1-indolinyl, 5-bromo-1-indolinyl, 2,7-dimethyl-1-indolinyl, 2-methyl-1-indolinyl, 5-bromo-7-nitro-1-indolinyl, 5-nitro-1-indolinyl, 2,3-dimethyl-1-indolinyl and the 6-nitro-1-indolinyl radicals.

Examples which may be mentioned of substituted 1,2,3,4-tetrahydroquinoline radicals are the 2-ethoxycarbonyl-1,2,3,4-tetrahydro-1-quinolinyl, 2-methyl-1,2,3,4-tetrahydro-1-quinolinyl, 6-methyl-1,2,3,4-tetrahydro-1-quinolinyl, 6-fluoro-2-methyl-1,2,3,4-tetrahydro-1-quinolinyl, 4-methyl-1,2,3,4-tetrahydro-1-quinolinyl, 8-amino-1,2,3,4-tetrahydro-1-quinolinyl and the 2-fluoro-6-methyl-1,2,3,4-tetrahydro-1-quinolinyl radicals.

Examples which may be mentioned of substituted 1,2,3,4-tetrahydroisoquinoline radicals are the 1-methyl-6,7-dihydroxy-1,2,3,4-tetrahydro-2-isoquinolinyl, 1-(3,4-dihydroxybenzyl)-6,7-dihydroxy-1,2,3,4-tetrahydro-2-isoquinolinyl, 3-carboxy-1,2,3,4-tetrahydro-2-isoquinolinyl, 6,7-dimethoxy-1,2,3,4-tetrahydro-2-isoquinolinyl, 1-benzyl-1,2,3,4-tetrahydro-2-isoquinolinyl, 1-(3-hydroxy-4-methoxybenzyl)-6-dimethylamino-1,2,3,4-tetrahydro-2-isoquinolinyl, 3-tert-butyl-6-methoxy-4-phenyl-1,2,3,4-tetrahydro-2-isoquinolinyl, 1-(3,4-dimethoxybenzyl)-6,7-dimethoxy-1,2,3,4-tetrahydro-2-isoquinolinyl, 1-(3,4-dihydroxybenzyl)-6,7-dihydroxy-1,2,3,4-tetrahydro-2-isoquinolinyl, 6,7-dihydroxy-1,2,3,4-tetrahydro-2-isoquinolinyl, 6,7-dimethoxy-1-methyl-1,2,3,4-tetrahydro-2-isoquinolinyl, 6,7-dihydroxy-1-methyl-1,2,3,4-tetrahydro-2-isoquinolinyl, 6-hydroxy-7-methoxy-1-methyl-1,2,3,4-tetrahydro-2-isoquinolinyl and the 1-(5-chloro-2-methylaminophenyl)-1,2,3,4-tetrahydro-2-isoquinolinyl radicals.

Suitable salts for compounds of the formula I in which n is the number 0 are all acid addition salts. Particular mention may be made of the pharmacologically suitable salts of the inorganic and organic acids which are customarily used in pharmaceutical technology. Pharmacologically unsuitable salts which may, for example, be the initial products of the process for preparing the compounds according to the invention on an industrial scale are converted into pharmacologically suitable salts by processes known to the skilled person. Suitable as such are water-soluble and water-insoluble acid addition salts with acids such as hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, with the acids being used in the preparation of the salts in a ratio of amounts which is equimolar or differs therefrom—depending on whether the acid is monobasic or polybasic and depending on which salt is required.

For compounds of the formula I in which n is the numbers 1 or 2, also suitable as salts are salts with bases. Examples which may be mentioned of basic salts are lithium, sodium, potassium, calcium, aluminum, magnesium, titanium, ammonium, meglumine or guanidinium salts, once again the ratio of the amounts of the bases used for preparing these salts being equimolar or differing therefrom.

Compounds of the formula I in which R1 is hydrogen, R2 is hydrogen, R3 is halogen and n is the number 0, and their salts, are to be emphasized.

Compounds of the formula I in which R1 is hydrogen, R2 is hydrogen, R3 is chlorine, R4 is 1-4C-alkyl, A is ethylene or propylene, X is CH and n is the number 0, and their salts, are to be particularly emphasized.

One embodiment within the compounds to be emphasized comprises compounds of the formula I in which R1 is hydrogen, R2 is hydrogen, R3 is halogen, R4 is 1-4C-alkyl, A is 2-4C-alkylene, X is N or CH and n is the number 0, and in which R5 is 1-4C-alkyl or Ar-1-4C-alkyl and R6 is Ar-1-4C-alkyl, where Ar is phenyl, furyl or phenyl which is substituted by R7, R8 and R9, or in which R5 and R6 together represent, with inclusion of the nitrogen atom to which both are bonded, an unsubstituted or substituted heterocyclic ring which is selected from the group consisting of piperidine, piperazine, 1,2,3,4-tetrahydroquinoline and 1,2,3,4-tetrahydroisoquinoline, where a substituted piperidino radical is substituted by one or two identical or different substituents selected from the group consisting of 1-4C-alkyl, 1-4C-alkoxy, phenyl, phenyl-1-4C-alkyl and phenyl substituted by R7, R8 and R9, a substituted piperazino radical is substituted in position 4 by a substituent selected from the group consisting of 1-4C-alkyl, 1-4C-alkoxycarbonyl, phenyl, phenyl substituted by R7, R8 and R9, phenyl-1-4C-alkyl, phenyl, 1-4C-alkyl substituted by R7, R8 and R9 in the phenyl radical, and benzhydryl a substituted 1,2,3,4-tetrahydroquinoline radical is substituted by one or two identical or different substituents selected from the group consisting of 1-4C-alkyl and halogen, a substituted 1,2,3,4-tetrahydroisoquinoline radical is substituted on the benzo moiety by one or two substituents selected from the group consisting of hydroxyl, 1-4C-alkoxy and di-1-4C-alkylamino, and where R7 is hydrogen, 1-4C-alkyl, 1-4C-alkoxy, halogen or nitro, R8 is hydrogen, 1-4C-alkyl, 1-4C-alkoxy, halogen or nitro, and R9 is hydrogen or trifluoromethyl, and the salts of these compounds.

One embodiment within the compounds to be particularly emphasized are compounds of the formula I in which R1 is hydrogen, R2 is hydrogen, R3 is chlorine, R4 is 1-4C-alkyl, A is ethylene or propylene, X is CH and n is the number 0, and in which R5 is 1-4C-alkyl or benzyl and R6 is Ar-1-4C-alkyl, where Ar is phenyl or furyl, or in which R5 and R6 together represent, with inclusion of the nitrogen atom to which both are bonded, an unsubstituted or substituted heterocyclic ring which is selected from the group consisting of piperidine, piperazine and 1,2,3,4-tetrahydroisoquinoline, where a substituted piperidino radical is substituted by a substituent selected from the group consisting of phenyl and benzyl, a substituted piperazino radical is substituted in position 4 by a substituent selected from the group consisting of phenyl, phenyl substituted by R7, R8 and R9, and benzyl and a substituted 1,2,3,4-tetrahydroisoquinoline radical is substituted on the benzo moiety by one or two 1-4C-alkoxy substituents, and where R7 is hydrogen or 1-4C-alkoxy, R8 is hydrogen and R9 is hydrogen, and the salts of these compounds.

The invention furthermore relates to a process for the preparation of the compounds of the formula I in which R1, R2, R3, R4, R5, R6, X, n and A have the abovementioned meanings, and their salts.

The process comprises a) reacting mercaptobenzimidazoles of formula II (see appended sheets of formulae) in which R1, R2 and X have the abovementioned meanings with picoline derivatives III (see appended sheet of formulae) in which R3, R4, R5, R6 and A have the abovementioned meanings, and Y is a suitable leaving group, or comprises b) reacting compounds of formula IV (see appended sheet of formulae) in which R1, R2, R3, R4, X, n and A have the abovementioned meanings, and Z is a suitable leaving group, with amines H—N(R5)R6 and (if compounds of formula I with n=1 or 2 are the required final products) comprises subsequently oxidizing the compounds with n=0 obtained as in a) or b), and/or comprises subsequently, if required, converting the compounds obtained into the salts and/or comprises subsequently, if required, converting salts obtained into the free compounds.

In the reaction detailed above, the starting compounds can be used as such or, where appropriate, in the form of their salts.

Examples of suitable leaving groups Y and Z which may be mentioned are halogen atoms, especially chlorine, or hydroxyl groups activated by esterification (for example with p-toluenesulfonic acid).

The reaction of II with III takes place in suitable, preferably polar protic or aprotic solvents (such as methanol, ethanol, isopropanol, dimethyl sulfoxide, acetone, dimethylformamide or acetonitrile) with addition or with exclusion of water. It is carried out, for example, in the presence of a proton acceptor. Suitable as, such are alkali metal hydroxides, such as sodium hydroxide; alkali metal carbonates, such as potassium carbonate; or tertiary amines, such as pyridine, triethylamine or ethyldiisopropylamine. Alternatively, the reaction can also be carried out without a proton acceptor, in which case—depending on the nature of the starting compounds—it is possible where appropriate for the acid addition salts to be initially separated off in particularly pure form. The reaction temperature can be between 0° and 150° C., with temperatures between 20° and 80° C. being preferred in the presence of proton acceptors, and between 60° and 120° C.—especially the boiling point of the solvent used—being preferred without proton acceptors. The reaction times are between 0.5 and 30 hours.

The reaction of the compounds IV with the amines H—N(R5)R6 takes place in a similar way to the reaction of the compounds II with the compounds III or, alternatively, preferably without additional solvent, using an excess of amine as proton acceptor and solvent simultaneously. The reaction temperature is in this case between 60° and 180° C., preferably between 80° and 160° C.

The oxidation of the sulfides (compounds of the formula I with n=0) to the sulfoxides or sulfones (compounds of the formula I with n=1 or 2) takes place under the conditions familiar to the skilled person for oxidizing sulfides to sulfoxides and sulfones [in this connection, see, for example, J. Drabowicz and M. Mikolajczyk, Organic preparations and procedures int. 14(1-2), 45–89(1982) or E. Block in S. Patai, The Chemistry of Functional Groups, Supplement E. Part 1, pages 539–608, John Wiley and Sons (Interscience Publication), 1980]. Suitable oxidizing agents are all reagents normally used for oxidizing sulfides to sulfoxides and sulfones, especially peroxy acids, such as, peroxyacetic acid, trifluoroperoxyacetic acid, 3,5-dinitroperoxybenzoic acid, peroxymaleic acid, magnesium monoperoxyphthalate or, preferably, m-chloroperoxybenzoic acid.

The reaction temperature is (depending on the reactivity of the oxidizing agent and degree of dilution) between −70° C. and the boiling point of the solvent used, but preferably between −30° and +20° C. Oxidation with halogens or with hypohalites (for example with aqueous sodium hypochlorite solution) has also proven advantageous, which is expediently carried out at temperatures between 0° and 50° C. The reaction is carried out, for example, in inert solvents, for example aromatic or chlorinated hydrocarbons, such as benzene, toluene, dichloromethane or chloroform, preferably in esters or ethers, such as ethyl acetate, isopropyl acetate or dioxane, or in alcohols, preferably isopropanol.

The sulfoxides according to the invention are optically active compounds. Further centers of chirality may also be present in the molecule depending on the nature of the substituents. The invention therefore embraces both the enantiomers and diastereomers and their mixtures and racemates. The enantiomers can be separated in a manner known per se (for example by preparation and separation of appropriate diastereoisomeric compounds) (see, for example, WO92/08716).

The compounds II are disclosed, for example, in DE 34 04 610 or EP 134 400. The compounds III can be prepared, for example, as described in the examples which follow or in analogy to EP 184 322.

The compounds of the formula IV can be prepared, for example, as described in the examples which follow from starting compounds which are known or can be obtained in an analogous manner.

The following examples illustrate the invention in detail without restricting it. The compounds according to the invention and the starting compounds can be prepared in a manner analogous to the description in the examples.

EXAMPLES

Final products 1. 2-{3-Chloro-4-{N-[2-(N-benzyl-N-ethylamino)ethyl]-N-methylamino}-2-pyridyl)-methylthio-1H-benzimidazole trihydrochloride 2-{3-Chloro-4-[N-(2-chloroethyl)-N-methylamino]-2-pyridyl}-methylthio-1H-benzimidazole (500 mg/1.24 mmol) are heated in N-ethylbenzylamine (15 ml) at 140° C. for 4.5 h. Then the excess N-ethylbenzylamine is removed by distillation under high vacuum, and the residue is chromatographed on silica gel (dichloromethane/methanol 97/3 mixture which contains 1 ml of conc. $NH_3 \times aq./l$). The collected pure fractions are concentrated together in vacuo and dissolved in a little methanol, and saturated ethereal hydrochloric acid (1 ml) and diisopropyl ether are added and the solid which precipitates thereby is filtered off and dried in vacuo. Yield: 200 mg (28%) of the title compound as a colorless solid of melting point >180° (decomposition).

2. 2-{3-Chloro-4-{N-[2-(1,2,3,4-tetrahydro-2-isoquinolinyl)ethyl]-N-methylamino}-2-pyridyl}-methylthio-1H-benzimidazole trihydrochloride 2-{3-Chloro-4-[N-2-chloroethyl)-N-methylamino]-2-pyridyl}-methylthio-1H-benzimidazole (500 mg) are heated in 1,2,3,4-tetrahydroisoquinoline (10 ml) at 100° C. for 2.5 h. The excess amine is removed by distillation under high vacuum, and the remaining oily residue is chromatographed on silica gel (petroleum ether/ethyl acetate/methanol 65/30/5-mixture which contains 1 ml of conc. $NH_3 \times aq./l$). The collected pure fractions are concentrated together in vacuo and dissolved in a little methanol (5 ml), and ethereal hydrochloric acid and then a little diisopropyl ether are added. The solid which precipitates thereby is filtered off and dried under high vacuum. Yield: 460 mg (65%) of the title compound as a colorless solid of melting point >240° C. (decomposition).

3. 2-{3-Chloro-4-{N-[2-(1,2,3,4-tetrahydro-2-isoquinolinyl)ethyl]-N-methylamino}-2-pyridyl}-methylthio-1H-benzimidazole 2-{3-Chloro-4-{N-[2-(4-1,2,3,4-tetrahydro-2-isoquinolinyl)ethyl]-N-methylamino}-2-pyridyl}-methylthio-1H-benzimidazole trihydrochloride (0.1 g) is dissolved in water (7 ml), and a saturated solution of aqueous sodium bicarbonate (1 ml). is added. The colorless precipitate produced thereby is filtered off, washed with distilled water and dried at 60° C. under high vacuum. Yield: 70 mg (87%) of the title compound of melting point >88° C. (decomposition).

4. 2-{3-Methyl-4-{N-{2-[N-(2-furfuryl)-N-methylamino]-ethyl}-N-methylamino}-2-pyridyl}-methylthio-1H-benzimidazole trihydrochloride In analogy to Example 1, 1.35 g (64%) of the title compound are obtained with a melting point of 212° C. (decomposition) by reacting 2-{3-chloro-4-[N-2-chloroethyl)-N-methylamino]-2-pyridyl}methylthio-1H-benzimidazole (1.5 g) with N-furfurylmethylamine (2 ml) after heating at 100° C. for 4 hours.

5. 2-{3-Chloro-4-{N-[2-(1,2,3,4-tetrahydro-2-isoquinolinyl)ethyl]-N-methylamino)-2-pyridyl}-methylthio-1H-imidazo[5,4-b]pyridine The title compound is obtained as a colorless powder of melting point 128°–129° C. (52%) by the procedure indicated in Example 2 starting from 2-{3-chloro-4-[N-(2-chloroethyl)-N-methylamino]-2-pyridyl}-methylthio-1H-imidazo[5,4-b]pyridine and 1,2,3,4-tetrahydroisoquinoline after chromatography on silica gel (ethyl acetate/methanol 4/1).

6. 2-{3-Chloro-4-{N-[2-(N-benzyl-N-methylamino)-ethyl]-N-methylamino}-2-pyridyl}-methylthio-1H-benzimidazole trihydrochloride The title compound is obtained as an amorphous powder of melting point 237°–240° C. (decomposition) by the procedure indicated in Example 1, by reacting 2-{3-chloro-4-[N-(2-chloroethyl)-N-methylamino]-2-pyridyl}-methylthio-1H-benzimidazole with N-methylbenzylamine and after purification on silica gel and subsequent conversion into the trichloride.

7. 2-{3-Chloro-4-{N-[2-(N,N-dibenzylamino)-ethyl]-N-methylamino}-2-pyridyl}-methylthio-1H-benzimidazole trihydrochloride The title compound is obtained as a colorless amorphous powder of melting point oil by the procedure indicated in Example 2, by reacting 2-{3-chloro-4-[N-(2-chloroethyl)-N-methylamino]-2-pyridyl}-methylthio-1H-benzimidazole with dibenzylamine after chromatography on silica gel (petroleum ether/ethyl acetate 1/1).

8. 2-{3-Chloro-4-{N-[2-(N,N-diethylamino)-ethyl]-N-methylamino}-2-pyridyl}-methylthio-1H-benzimidazole trihydrochloride The title compound is obtained as an amorphous powder of melting point 245.7° C. (decomposition) by the procedure indicated in Example 1, by reacting 2-{3-chloro-4-[N-2-chloroethyl)-N-methylamino]-2-pyridyl}-methylthio-1H-benzimidazole with diethylamine after chromatography on silica gel (ethyl acetate/methanol 4/1) and subsequent conversion into the trihydrochloride.

9. 2-{3-Chloro-4-{N-[2-(N-methyl-N-phenethylamino)-ethyl]-N-methylamino}-2-pyridyl}-methylthio-1H-benzimidazole trihydrochloride The title compound is obtained as an amorphous powder of melting point 239°–241° C. (decomposition) by the procedure indicated in Example 1, by reacting 2-{3-chloro-4-[N-(2-chloroethyl)-N-methylamino]-2-pyridyl}-methylthio-1H-benzimidazole with N-methylphenethylamine after purification on silica gel (ethyl acetate/methanol 9/1) and subsequent conversion into the trihydrochloride.

10. 2-{3-Chloro-4-{N-[2-(N-furfuryl-N-methylamino)ethyl]-N-methylamino}-2-pyridyl}-methylthio-1H-benzimidazole trihydrochloride The title compound is obtained as a brownish amorphous powder of melting point 239°–241° C. (decomposition) by the procedure indicated in Example 1, by reacting 2-{3-chloro-4-[N-(2-chloroethyl)-N-methylamino]-2-pyridyl}-methylthio-1H-benzimidazole with N-furfurylmethylamine after chromatography on silica gel (ethyl acetate/methanol 9/1) and subsequent conversion into the trihydrochloride.

11. 2-{3-Chloro-4-{N-[2-(4-phenyl-piperidino)-ethyl]-N-methylamino}-2-pyridyl}-methylthio-1H-benzimidazole The title compound is obtained as an amorphous yellowish powder of melting point 55°–65° C. by the procedure indicated in Example 2, by reacting 2-{3-chloro-4-[N-(2-chloroethyl)-N-methylamino]-2-pyridyl}-methylthio-1H-benzimidazole with 4-phenylpiperidine after purification on silica gel (ethyl acetate/methanol 3/1).

12. 2-{3-Chloro-4-{N-[2-(4-benzyl-piperidino)-ethyl]-N-methylamino}-2-pyridyl}-methylthio-1H-benzimidazole The title compound is obtained as a viscous, yellowish oil by the procedure indicated in Example 2, by reacting 2-{3-chloro-4-[N-(2-chloroethyl)-N-methylamino]-2-pyridyl}-methylthio-1H-benzimidazole with 4-benzylpiperidine after purification on silica gel (ethyl acetate/methanol 4/1).

13. 2-{3-Chloro-4-[N-(2-piperidinoethyl)-N-methylamino]-2-pyridyl}-methylthio-1H-benzimidazole The title compound is obtained as a viscous brownish oil by the procedure indicated in Example 2, by reacting 2-{3-chloro-4-[N-(2-chloroethyl)-N-methylamino]-2-pyridyl}-methylthio-1H-benzimidazole with piperidine after chromatography on silica gel (ethyl acetate/methanol 4/1).

14. 2-{3-Chloro-4-{N-[2-(6,7-dimethoxy-1,2,3,4-tetrahydro-2-isoquinolinyl)ethyl]-N-methylamino}-2-pyridyl}-methylthio-1H-benzimidazole The title compound is obtained as a viscous yellowish oil by the procedure indicated in Example 2, by reacting 2-{3-chloro-4-[N-(2-chloroethyl)-N-methylamino]-2-pyridyl}-methylthio-1H-benzimidazole with 6,7-dimethoxy-1,2,3,4-tetrahydroisoquinoline after chromatography on silica gel (ethyl acetate/methanol 4/1).

15. 2-{3-Chloro-4-{N-[2-(4-phenylpiperazino)-ethyl]-N-methylamino}-2-pyridyl}-methylthio-1H-benzimidazole hydrochloride The title compound is obtained as an amorphous powder of melting point 212°–215° C. (decomposition) by the procedure indicated in Example 1, by reacting 2-{3-chloro-4-[N-(2-chloroethyl)-N-methylamino]-2-pyridyl}-methylthio-1H-benzimidazole with 4-phenylpiperazine after chromatography on silica gel (ethyl acetate/methanol 4/1) and subsequent conversion into the hydrochloride.

16. 2-{3-Chloro-4-{N-[2-(4-benzylpiperazino)-ethyl]-N-methylamino}-2-pyridyl}-methylthio-1H-benzimidazole trihydrochloride The title compound is obtained as an amorphous powder of melting point 227°–230° C. (decomposition) by the procedure indicated in Example 1, by reacting 2-{3-chloro-4-[N-(2-chloroethyl)-N-methylamino]-2-pyridyl}-methylthio-1H-benzimidazole with 4-benzylpiperazine after chromatography on silica gel (ethyl acetate/methanol 4/1) and subsequent conversion into the trihydrochloride.

17. 2-{3-Chloro-4-{N-[2-(4-(2-methoxyphenyl)-piperazino)-ethyl]-N-methylamino}-2-pyridyl}-methylthio-1H-benzimidazole trihydrochloride The title compound is obtained as a viscous oil by the procedure indicated in Example 1, by reacting 2-{3-chloro-4-[N-(2-chloroethyl)-N-methylamino-2-pyridyl}-methylthio-1H-benzimidazole with 4-(2-methoxyphenyl)piperazine after purification on silica gel (ethyl acetate/methanol 9/1).

18. 2-{3-Chloro-4-{N-[3-(1,2,3,4-tetrahydro-2-isoquinolinyl)-propyl]-N-methylamino}-2-pyridyl}-methylthio-1H-benzimidazole trihydrochloride The title compound of melting point 239°–240° C. (decomposition) is obtained in analogy to Example 2 by reacting 2-{3-chloro-4-[N-(3-chloropropyl)-N-methylamino]-2-pyridyl}-methylthio-1H-benzimidazole with 1,2,3,4-tetrahydroisoquinoline and conversion into the trihydrochloride.

19. 2-{3-Chloro-4-{N-[3-(N-benzyl-N-methylamino)propyl]-N-methylamino}-2-pyridyl}-methylthio-1H-benzimidazole trihydrochloride The title compound is obtained as an amorphous powder of melting point 228°–230° C. (decomposition) by the procedure indicated in Example 1, by reacting 2-{3-chloro-4-[N-(3-chloropropyl)-N-methylamino]-2-pyridyl}-methylthio-1H-benzimidazole with N-methylbenzylamine after purification on silica gel and subsequent conversion into the trihydrochloride.

20. 2-{3-Chloro-4-{N-[3-(6,7-dimethoxy-1,2,3,4-tetrahydro-2-isoquinolinyl)-propyl]-N-methylamino}-2-pyridyl}-methylthio-1H-benzimidazole trihydrochloride The title compound is obtained as a viscous yellowish oil by the procedure indicated in Example 1, by reacting 2-{3-chloro-4-[N-(3-chloropropyl)-N-methylamino]-2-pyridyl)-methylthio-1H-benzimidazole with 6,7-dimethoxy-1,2,3,4-tetrahydroisoquinoline after chromatography on silica gel (petroleum ether/ethyl acetate/methanol 2/5/1).

21. 2-{3-Chloro-4-{N-[3-(4-benzyl-piperidino)-propyl]-N-methylamino}-2-pyridyl}-methylthio-1H-benzimidazole trihydrochloride The title compound is obtained as a viscous, yellowish oil by the procedure indicated in Example 1, by reacting 2-{3-chloro-4-[N-(3-chloropropyl)-N-methylamino]-2-pyridyl}- methylthio-1H-benzimidazole with 4-benzylpiperidine after purification on silica gel (ethyl acetate/methanol 4/1) and conversion into the trihydrochloride.

Precursors

A. 2-{3-Chloro-4-[N-(2-chloroethyl)-N-methylamino]-2-pyridyl}-methylthio-1H-benzimidazole dihydrochloride 1) 3-Chloro-4-[N-(2-hydroxyethyl)-N-methylamino]-2-hydroxymethylpyridine A mixture of 3,4-dichloro-2-hydroxymethylpyridine (J. Med. Chem. 1989, 32, 1970) (2.5 g) in 2-methylaminoethanol (30 ml) is heated at 160° C. in a steel autoclave for 2.5 h, the excess amine is stripped off under high vacuum, and the remaining residue is chromatographed on silica gel (dichloromethane/methanol 95/5). Yield: 2.3 g as yellowish oil.

2) 3-Chloro-4-[N-(2-chloroethyl)-N-methylamino]-2-chloromethylpyridine hydrochloride A solution of thionyl chloride (4 ml) in dichloromethane (20 ml) is added dropwise to a solution of 3-chloro-4-[N-(2-hydroxyethyl)-N-methylamino]-2-hydroxymethylpyridine (2.3 g) in dichloromethane (30 ml) at 0° C. The temperature is then allowed to rise to 20° C. (20 min), and then the temperature is kept at 40° C. for 30 min. The solvent is stripped off in vacuo and then the remaining residue is chromatographed on silica gel (petroleum ether/ethyl acetate 7/3 mixture which contains 1 ml of conc. $NH_3 \times aq/l$). Yield: 2.6 g.

3) A mixture of 2-mercapto-1H-benzimidazole (1.8 g) and 3-chloro-4-[N-(2-chloroethyl)-N-methylamino]-2-chloromethylpyridine hydrochloride (1.1 g) in isopropanol (40 ml) is boiled for 1.5 h, the solvent is stripped off in vacuo until the volume is 20 ml, and diisopropyl ether (20 ml) is added to this solution. The crystals which precipitate after some time are filtered off and dried in vacuo. Yield: 1.2 g of the title compound of melting point 202° C. (decomposition).

2-{3-Chloro-4-[N-(3-chloropropyl)-N-methylamino]-2-pyridyl}-methylthio-1H-benzimidazole dihydrochloride is obtained in an analogous manner.

B. 2-{3-Chloro-4-[N-(2-chloroethyl)-N-methylamino]-2-pyridyl}-methylthio-1H-imidazo[5,4-b]pyridine A mixture of 3-chloro-4-[N-(2-chloroethyl)-N-methylamino]-3-chloromethylpyridine hydrochloride (0.96 g) and 2-mercapto-1H-imidazo[5,4-b]pyridine (0.5 g) in isopropanol (25 ml) is heated at 90° C. for 4 h, and the reaction mixture is then cooled to 0° C. The crystals which have precipitated are filtered off and washed with a little cold isopropanol. The filter cake is dissolved in water (30 ml), saturated aqueous sodium bicarbonate solution (20 ml) is added to the solution, and the mixture is extracted with dichloromethane. The collected extracts are evaporated to dryness in vacuo, and the remaining crystalline residue is dried under high vacuum. Yield: 0.68 g of the title compound of melting point 184°–185° C.

Susceptibility of Industrial Application

The excellent activity of compounds of the formula I and their salts on helicobacter bacteria makes it possible for them to be used in human medicine as active substances for the treatment of diseases based on helicobacter bacteria.

The invention therefore furthermore relates to a method for the treatment of mammals, especially humans, suffering from diseases based on helicobacter bacteria. The method comprises administering a therapeutically effective and pharmacologically suitable amount of one or more compounds of formula I and/or of their pharmacologically suitable salts to the individual with the disease.

The invention additionally relates to the compounds of the formula I and their pharmacologically suitable salts for use for the treatment of diseases based on helicobacter bacteria.

The invention likewise embraces the use of compounds of formula I and of their pharmacologically suitable salts for producing pharmaceuticals used to control diseases based on helicobacter bacteria.

The invention furthermore relates to pharmaceuticals for controlling helicobacter bacteria, which contain one or more compounds of the general formula I and/or their pharmacologically suitable salts.

Of the helicobacter strains on which the compounds of the formula I prove to be effective, particular mention may be made of the strain *Helicobacter pylori*.

The pharmaceuticals are produced by processes known per se and familiar to the skilled person. As pharmaceuticals, the pharmacologically active compounds of the formula I and their salts (=active substances) are used either as such or, preferably, in combination with suitable pharmaceutical ancillary substances, for example in the form of tablets, coated tablets, capsules, emulsions, suspensions, gels or solutions, where the content of active substance is preferably between 0.1 and 95%.

The ancillary substances suitable for the required pharmaceutical formulations are familiar to the skilled person on the basis of his expert knowledge. Besides solvents, gel formers, tablet ancillary substances and other active substance vehicles, it is possible to use, for example, antioxidants, dispersants, emulsifiers, antifoam agents, masking flavors, preservatives, solubilizers, colorants or permeation promoters and complexing agents (for example cyclodextrins).

The active substances can be administered, for example, parenterally (for example intravenously) or, in particular, orally.

In general, the active substances are administered in human medicine in a daily dose of about 0.2 to 50, preferably 1 to 30, mg/kg of bodyweight, where appropriate in the form of several, preferably 2 to 6, individual doses to achieve the desired result.

In this connection, it should particularly be mentioned as an aspect essential to the invention that the compounds of the formula I in which n is the number 0 prove to be active on helicobacter bacteria even on administration of doses which are below the doses which would have to be used to achieve an inhibition—sufficient for therapeutic purposes—of gastric acid secretion.

Compounds of the formula I in which n is the number 1 also have—besides their activity on helicobacter bacteria—a pronounced inhibitory effect on gastric acid secretion. Accordingly, these compounds can also be used to treat diseases based on increased gastric acid secretion.

Biological Investigations

The compounds of the formula I were investigated for their activity on *Helicobacter pylori* by methods based on those described by Tomoyuki Iwahi et al. (Antimicrobial. Agents and Chemotherapy, 1991, 490–496) using Columbia agar (Oxoid) and with a growth period of 4 days. The investigated compounds were found thereby to have the MIC values listed in the following table (the stated numbers of the compounds agree with the compound numbers in the description).

TABLE

| Compound No. | MIC-Value (μg/ml) |
|---|---|
| 1 | <1 |
| 2 | <1 |
| 3 | <1 |
| 4 | <1 |
| 5 | <1 |
| 6 | <1 |
| 9 | <1 |
| 10 | <1 |
| 11 | <1 |
| 12 | <1 |
| 13 | <1 |
| 14 | <1 |
| 15 | <1 |
| 16 | <1 |
| 17 | <1 |
| 18 | <1 |
| 19 | <1 |
| 20 | <1 |
| 21 | <1 |

SHEET OF FORMULAE

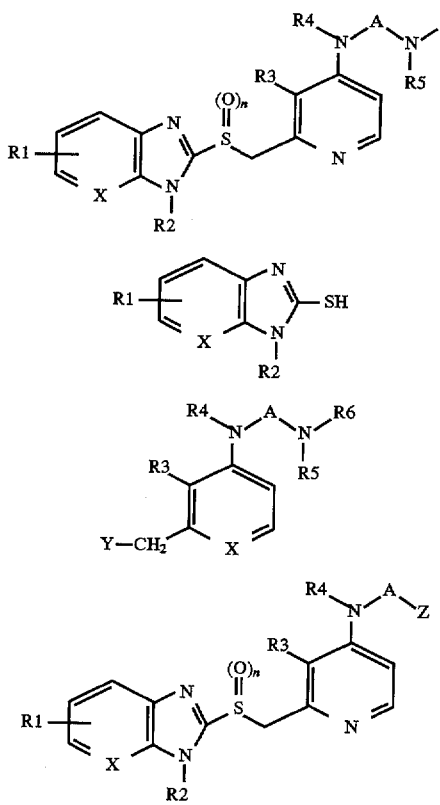

I claim:

1. A compound of formula I

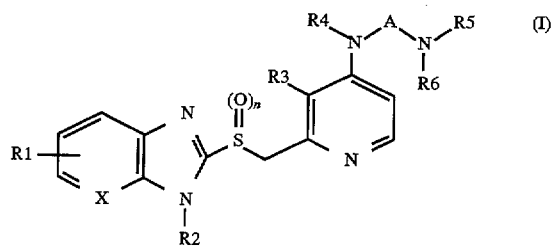

in which

R1 is hydrogen, 1-4C-alkyl, 1-4C-alkoxy, halogen, trifluoromethyl, wholly or predominantly fluorine-substituted 1-4C-alkoxy, chlorodifluoromethoxy or 2-chloro-1,1,2-trifluoroethoxy, R2 is hydrogen or 1-4C-alkyl, R3 is halogen or 1-4C-alkyl, R4 is 1-7C-alkyl, A is 1-7C-alkylene, X is N or CH, and n is the number 0, 1 or 2, and in which R5 is 1-7C-alkyl, 3-8C-cycloalkyl or Ar-1-4C-alkyl and R6 is 1-7C-alkyl, 3-8C-cycloalkyl or Ar-1-4C-alkyl, where Ar is phenyl, furyl, naphthyl, tetrahydronaphthyl, or phenyl which is substituted by R7, R8 and R9, or in which R5 and R6 together represent, with inclusion of the nitrogen atom to which both are bonded, an unsubstituted or substituted heterocyclic ring which is selected from the group consisting of pyrrolidine, piperidine, piperazine, morpholine, indoline, octahydro-1H-indole, 1,2,3,4-tetrahydroquinoline, 1,2,3,4-tetrahydroisoquinoline, decahydroquinoline and decahydroisoquinoline, where a substituted pyrrolidino radical is substituted by one or two identical or different substituents selected from the group consisting of 1-4C-alkyl, 1-4C-alkoxy, 1-4C-alkoxy-1-4C-alkyl, 1-4C-alkoxycarbonyl, 1-4C-alkylcarbonyloxy, hydroxy-1-4C-alkyl, hydroxyl and carboxyl, a substituted piperidino radical is substituted by one, two or three identical or different substituents selected from the group consisting of 1-4C-alkyl, gem.-di-1-4C-alkyl, 1-4C-alkoxy, 1-4C-alkoxy-1-4C-alkyl, 1-4C-alkoxycarbonyl, 1-4C-alkylcarbonyl, 1-4C-alkylcarbonyl-1-4C-alkyl, hydroxy-1-4C-alkyl, dihydroxy-1-4C-alkyl, di-1-4C-alkylamino, di-1-4C-alkylamino-1-4C-alkyl, pyrrolidino, piperidino, pyrrolidinyl-1-4C-alkyl, piperidinyl-1-4C-alkyl, carbamoyl, di-1-4C-alkylaminocarbonyl, piperidinocarbonyl, morpholinocarbonyl, phenyl, phenyl substituted by R7, R8 and R9, phenyl-1-4C-alkyl, benzoyl, benzoyl substituted by halogen, or formyl, carboxyl, cyano, hydroxyl, halogen and sulfo, a substituted piperazino radical can be substituted in position 2, 3, 5 or 6 by a 1-4C-alkyl radical and is substituted in position 4 by a substituent selected from the group consisting of 1-4C-alkyl, 3-7C-cycloalkyl, 3-7C-cycloalkyl-1-4C-alkyl, 1-4C-alkoxycarbonyl, 1-4C-alkoxycarbonyl-1-4C-alkyl, hydroxy-1-4C-alkyl, di-1-4C-alkylamino-1-4C-alkyl, halo-1-4C-alkyl, carbamoyl, phenyl, phenyl substituted by R7, R8 and R9, phenyl-1-4C-alkyl, phenyl-1-4C-alkyl substituted by R7, R8 and R9 in the phenyl radical, naphthyl, benzhydryl and benzhydryl substituted by halogen, a substituted morpholino radical is substituted by one or two identical or different 1-4C-alkyl radicals, a substituted 1-indolinyl radical can be substituted in position 2 and/or 3 by a carboxyl group or by one or two identical or different 1-4C-alkyl radicals, and can be substituted in the benzo moiety by one or two identical or different substituents selected from the group consisting of 1-4C-alkyl, halogen and nitro, a substituted 1,2,3,4-tetrahydroquinoline radical is substituted by one or two identical or different substituents selected from the group consisting of 1-4C-alkyl and halogen, a substituted 1,2,3,4-tetrahydroisoquinoline radical can be substituted on positions 1, 3 and/or 4 by one or two identical or different substituents selected from the group consisting of 1-4C-alkyl, carboxyl, phenyl, phenyl-1-4C-alkyl or phenyl which is substituted by R7, R8 and R9 in the phenyl radical, and can be substituted on the benzo moiety by one or two substituents selected from the group consisting of hydroxyl, 1-4C-alkoxy and di-1-4C-alkylamino, and where R7 is hydrogen, 1-4C-alkyl, 1-4C-alkoxy, 1-4C-alkylcarbonyl, halogen, 1-4C-alkylamino or nitro, R8 is hydrogen, 1-4C-alkyl, 1-4C-alkoxy, halogen or nitro, and R9 is hydrogen or trifluoromethyl, or a salt thereof.

2. A compound of formula I as claimed in claim 1, in which R1 is hydrogen, R2 is hydrogen, R3 is halogen and n is the number 0, or a salt thereof.

3. A compound of formula I as claimed in claim 1, in which R1 is hydrogen, R2 is hydrogen, R3 is chlorine, R4 is 1-4C-alkyl, A is ethylene or propylene, X is CH and n is the number 0, or a salt thereof.

4. A compound of the formula I as claimed in claim 1, in which R1 is hydrogen, R2 is hydrogen, R3 is halogen, R4 is 1-4C-alkyl, A is 2-4C-alkylene, X is N or CH and n is the number 0, and in which R5 is 1-4C-alkyl or Ar-1-4C-alkyl and R6 is Ar-1-4C-alkyl, where Ar is phenyl, furyl or phenyl which is substituted by R7, R8 and R9, or in which R5 and R6 together represent, with inclusion of the nitrogen atom to which both are bonded, an unsubstituted or substituted heterocyclic ring which is selected from the group consisting of piperidine, piperazine, 1,2,3,4-tetrahydroquinoline and 1,2,3,4-tetrahydroisoquinoline, where a substituted piperidino radical is substituted by one or two identical or different substituents selected from the group consisting of 1-4C-alkyl, 1-4C-alkoxy, phenyl, phenyl-1-4C-alkyl and phenyl substituted by R7, R8 and R9, a substituted piperazino radical is substituted in position 4 by a substituent selected from the group consisting of 1-4C-alkyl, 1-4C-alkoxycarbonyl, phenyl, phenyl substituted by R7, R8 and R9, phenyl-1-4C-alkyl, phenyl-1-4C-alkyl substituted by R7, R8 and R9 in the phenyl radical, and benzhydryl a substituted 1,2,3,4-tetrahydroquinoline radical is substituted by one or two identical or different substituents selected from the group consisting of 1-4C-alkyl and halogen, a substituted 1,2,3,4-tetrahydroisoquinoline radical is substituted on the benzo moiety by one or two substituents selected from the group consisting of hydroxyl, 1-4C-alkoxy and di-1-4C-alkylamino, and where R7 is hydrogen, 1-4C-alkyl, 1-4C-alkoxy, halogen or nitro, R8 is hydrogen, 1-4C-alkyl, 1-4C-alkoxy, halogen or nitro, and R9 is hydrogen or trifluoromethyl, or a salt thereof.

5. A compound of formula I as claimed in claim 1, in which R1 is hydrogen, R2 is hydrogen, R3 is chlorine, R4 is 1-4C-alkyl, A is ethylene or propylene, X is CH and n is the number 0, and in which R5 is 1-4C-alkyl or benzyl and R6 is Ar-1-4C-alkyl, where Ar is phenyl or furyl, or in which R5 and R6 together represent, with inclusion of the nitrogen atom to which both are bonded, an unsubstituted or substituted heterocyclic ring which is selected from the group consisting of piperidine, piperazine and 1,2,3,4-tetrahydroisoquinoline, where a substituted piperidino radical is substituted by a substituent selected from the group consisting of phenyl and benzyl, a substituted piperazino radical is substituted in position 4 by a substituent selected from the group consisting of phenyl, phenyl substituted by R7, R8 and R9, and benzyl and a substituted 1,2,3,4-tetrahydroisoquinoline radical is substituted on the benzo moiety by one or two 1-4C-alkoxy substituents, and where R7 is hydrogen or 1-4C-alkoxy, R8 is hydrogen and R9 is hydrogen, or a salt thereof.

6. A process for the preparation of a compound of formula I as claimed in claim 1, in which R1, R2, R3, R4, R5, R6, X, n and A have the meanings stated in claim 1, and a salt thereof, which comprises a) reacting a mercaptobenzimidazole of the formula II

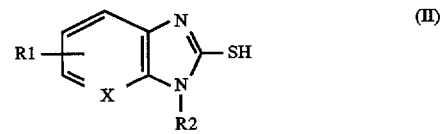

in which R1, R2 and X have the meanings stated in claim 1, with a picoline derivative III

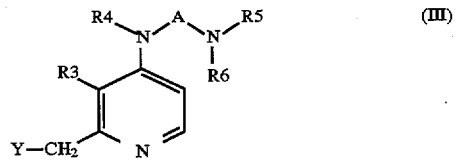

in which R3, R4, R5, R6 and A have the meanings stated in claim 1, and Y is a suitable leaving group, or comprises b) reacting a compound of the formula IV

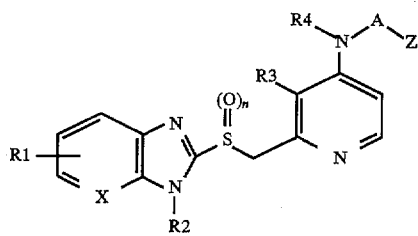

in which R1, R2, R3, R4, X, n and A have the meanings stated in claim 1, and Z is a suitable leaving group, with an amine H—N(R5)R6 and (if a compound of the formula I with n=1 or 2 is the required final product) comprises subsequently oxidizing the compound with n=0 obtained as in a) or b), and/or comprises subsequently, if required, converting the compound obtained into a salt thereof and/or comprises subsequently, if required, converting a salt obtained into the free compound.

7. A pharmaceutical comprising one or more compounds of formula I as claimed in claim 1 and/or pharmacologically suitable salt thereof.

8. A pharmaceutical composition comprising a suitable carrier and an effective amount of a compound of claim 1 or a pharmacologically suitable salt thereof.

9. In a method for controlling Helicobacter bacteria with an effective amount of an active ingredient, the improvement wherein the active ingredient is a compound of claim 1 or a pharmacologically suitable salt thereof.

10. In a method for treatment and/or prophylaxis of a disorder of the stomach and/or of the intestine with an effective amount of an active ingredient, the improvement wherein the active ingredient is a compound of claim 1 or a pharmacologically suitable salt thereof.

11. A method for treatment and/or prophylaxis of a disorder of the stomach and/or of the intestine based on increased gastric acid secretion, which comprises administering to a subject, prone to or afflicted with such disorder, an effective amount of a compound of claim 1, in which n is the number 1, or a pharmacologically suitable salt thereof.

* * * * *